United States Patent
Kunz

(10) Patent No.: US 7,687,276 B2
(45) Date of Patent: Mar. 30, 2010

(54) METHOD OF DETECTING ANALYTE VAPORIZED FROM SAMPLE WITH LOW-POWER UV RADIATION

(75) Inventor: Roderick R. Kunz, Acton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1168 days.

(21) Appl. No.: 10/443,141

(22) Filed: May 22, 2003

(65) Prior Publication Data

US 2005/0079626 A1 Apr. 14, 2005

Related U.S. Application Data

(60) Provisional application No. 60/383,811, filed on May 30, 2002.

(51) Int. Cl.
    *G01N 21/00* (2006.01)
(52) U.S. Cl. .................. 436/164; 436/166; 436/172
(58) Field of Classification Search .................. None
    See application file for complete search history.

(56) References Cited

U.S. PATENT DOCUMENTS

| | | | |
|---|---|---|---|
| 3,463,591 A * | 8/1969 | Franken et al. ............... 356/318 |
| 4,220,414 A * | 9/1980 | Barringer ..................... 356/318 |
| 4,468,468 A | 8/1984 | Benninghoven et al. |
| 5,083,019 A * | 1/1992 | Spangler ..................... 250/286 |
| 5,521,381 A | 5/1996 | Gregg et al. |
| 6,323,482 B1 | 11/2001 | Clemmer et al. |
| 6,368,558 B1 | 4/2002 | Suslick et al. |
| 6,495,823 B1 | 12/2002 | Miller et al. |

FOREIGN PATENT DOCUMENTS

| | | | |
|---|---|---|---|
| DE | 19934561 A1 * | 2/2001 |
| JP | 08184538 A * | 7/1996 |
| WO | WO 01/93305 | 12/2001 |

OTHER PUBLICATIONS

Moenke-Blankenburg et al. "Processes of laser ablation and vapor transport to the ICP" Special Publication—Royal Society of Chemistry (1990), 85(Plasma Source Mass Spectrom.), 1-17, Abstract.*
Grotemeyer et al. "Biomolecules in the Gas Phase. Multiphoton-Ionization Mass Spectrometry of Native Chlorophylls", J. Am. Cherm. Soc., 1986, v. 108, pp. 4233-4234.*
Akiyoshi et al. JP 408,184,538 A, computer translation.*
Groom "High resolution silicon detector for 1.2{3.1 eV (400{1000 nm) photons",. 2004 http://www.pg.infn.it/calor/2004/program/pres/monday_afternoon/groom.pdf.*

(Continued)

*Primary Examiner*—Yelena G Gakh
(74) *Attorney, Agent, or Firm*—Fish & Richardson P.C.

(57) ABSTRACT

A method for collecting and concentrating trace chemicals for subsequent analysis by virtually any type of chemical detector includes providing directed radiation to a sample, or a portion of a sample. An apparatus can include a sampling body for providing radiation.

32 Claims, 8 Drawing Sheets

Sample:

Woman's high-heel shoe with:
  250 ng DNT
  250 ng PETN
  250 ng RDX
placed on the arch of the sole Two sample acquisitions:
  No VUV irradiation
  With VUV irradiation
    $\lambda$=172 nm
    $\Phi$~20 mW/cm$^2$ Sample acquisition time: 10 min.
Sample acquisition geometry highly unoptimized (Data shown is GCMS single-ion chromatogram at m/e=61)

OTHER PUBLICATIONS

PCT International Search Report for a counterpart application.

*Laser desorption-ionization of polycyclic aromatic hydrocarbons from glass surfaces with ion mobility spectrometry analysis*, Young, D., et al. *Analytica Chimica Acta* (2002) 453 (2):231-243.

"Field detection of bacillus spore aerosols with stand-alone pyrolysis-gas-chromatography-ion mobility spectrometry" by Snyder, A.P., et al., *Field Analytical Chemistry and Technology* (1999) 3(4-5):315-326.

"Method for the Determination of Volatile Organic Compounds in Ambient Air suing Tenax® Adsorption and Gas Chromatorgraphy/Mass Spectrometry (GC/MS)." E.P.A. Analytical Methods TO-1; Revision 1.0, (Apr. 1984).

Creaser et al., "In-Membrane Preconcentration/Membrane Inlet Mass Spectrometry of Volatile and Semivolatile Organic Compounds" Anal. Chem. 72:2730-2736 (2000).

Krost et al., "Collection and Analysis of Hazardous Organic Emissions" Anal. Chem., 54:810-817 (1982).

McClenny et al., "Compendium of Methods for the Determination of Toxic Organic Compounds in Ambient Air." E.P.A. Analytical Methods TO-15; $2^{nd}$ Ed., Center for Environ. Res. Info. Office of Res. Devel. EPA, Cincinnati, OH (Jan. 1999).

* cited by examiner (Data shown is GCMS single-ion chromatogram at m/e=61)

Sample:

Cotton fabric:
  25 µg RDX
  applied via liquid solution
  and dried into the fabric Two sample acquisitions:
  No VUV irradiation
  With VUV irradiation
    λ=157 nm
    Φ~8 mW/cm²

Sample acquisition time: 10 min.
Complete headspace gas was analyzed (Data shown is GCMS single-ion chromatogram at m/e=61)

US 7,687,276 B2

METHOD OF DETECTING ANALYTE VAPORIZED FROM SAMPLE WITH LOW-POWER UV RADIATION

CLAIM OF PRIORITY

This application claims priority under 35 USC §119(e) to U.S. Patent Application Ser. No. 60/383,811, filed on May 30, 2002, which is incorporated by reference in its entirety.

FEDERALLY SPONSORED RESEARCH OR DEVELOPMENT

The U.S. Government may have certain rights in this invention pursuant to Grant No. F19628-00-C-0002 awarded by the Department of the Air Force.

TECHNICAL FIELD

This invention relates to a chemical sampler.

BACKGROUND

Identification of low levels of chemicals found outside the laboratory can provide valuable information for counter-terrorism efforts, crime scene investigations, law enforcement, forensics, and environmental chemistry, among many others. An important element of trace chemical detection is the sampling method, which can be described as the interface between the chemical detector and the environment. Since many types of trace chemicals such as fire accelerants, explosive residues, narcotics, toxic pollutants, and chemical warfare agents exhibit very low vapor pressures, some form of energy must be applied to these molecules as part of the sampling method to ensure that their abundance in the gas phase as they exit the sampler and enter the detector is sufficiently high to be detected. Common forms of energy employed in existing chemical samplers include mechanical samplers, which utilize directed air flow and/or surface wiping (as in common airport portal sensors), or thermal energy samplers, for example, heat samplers.

SUMMARY

A device and method for gathering chemical samples for the purpose of analyzing their identities and compositions is described. An apparatus and method for sampling a chemical involve applying directed radiation to enhance the vaporization rates of molecules physically or chemically bound on surfaces thereby increasing the rate at which the molecules can be introduced into a detection instrument.

In one aspect, a method of analyzing a sample includes applying radiation to a sample in contact with a vaporization space, and detecting an analyte in the vaporization space. In another aspect, a method of analyzing a sample includes applying UV or VUV radiation to a sample in contact with a vaporization space to vaporize an analyte, concentrating the analyte, and detecting the analyte with a detector.

The radiation can be UV or VUV radiation. The vaporization space can be at ambient pressure. The vaporization space can be at a temperature less than 100° C. Applying radiation can include irradiating the sample with a non-laser radiation source or a laser radiation source. The method can include vaporizing the analyte from the sample to form an analyte vapor. The method can include concentrating the analyte vapor before detecting the analyte. A charge of a molecule of the analyte vapor can be the same as a charge of a molecule of the analyte. The method can include transporting the analyte vapor to a detector with a carrier gas. The carrier gas can be air or an inert gas. The sample can be an article of commerce. The sample can include a non-volatile material. The radiation can be applied from a radiation source in a sampling unit, the sampling unit including the vaporization space. The sampling unit can be portable. The detector can include an ion mobility spectrometer, a surface acoustic wave device, an artificial nose, a gas chromatograph, a chemiluminescence detector, a fluorescence detector, a fluorescence-quenching detector, a flame ionization detector, a flame photometric detector, or an infrared spectrometer. The sample can include paper, wood, plastic, metal, or fabric. The sample can be an article of clothing. The analyte can be a drug, an explosive, a residue of an explosive, a poison, or a pollutant. The sample can include an aerosol particle. The method can include collecting an aerosol particle on a surface to form a sample.

In another aspect, an apparatus includes a sampling unit including a radiation source and a vaporization space including a sample, and a detector in vapor communication with the vaporization space. The radiation source can include a source of UV or VUV radiation. The radiation source can include a lamp or a laser. The vaporization space can be at ambient pressure. The vaporization space can be at a temperature less than 100° C. The sampling unit can be portable. The detector can be portable. The apparatus can include a carrier gas source. The carrier gas source can include a source of air or a source of inert gas. The vaporization space can be configured to be positioned over the sample. The apparatus can include an aerosol particle impactor. The apparatus can include a preconcentrator in vapor communication with the vaporization space and the detector. The detector can be separated from the sampling body by a vapor conduit configured to communicate vapor between the vaporization space and the detector. The detector can include an ion mobility spectrometer, a surface acoustic wave device, an artificial nose, a gas chromatograph, a chemiluminescence detector, a fluorescence detector, a fluorescence-quenching detector, a flame ionization detector, a flame photometric detector, or an infrared spectrometer.

Application of radiation at photon energies greater than the thermal energy accessible by heating allows photo-vaporization of molecules that are too strongly bound to surfaces to be vaporized by simple heating. Such molecules can include chemicals which possess very high heats of vaporization or those chemicals bound to surfaces through covalent interactions. Use of directed radiation can allow for spatially selective sampling of chemicals and allow for trace chemical analysis in locations where application of conventional mechanical or thermal forms of energy is too difficult. Such spaces can include the surfaces of large objects, large-area fabrics, or even an individual's clothing.

The directed radiation can be localized on the surface of a sample. The radiation can be between the wavelengths 100 and 400 nanometers, which fall in the vacuum ultraviolet (VUV) and ultraviolet (UV) portions of the electromagnetic spectrum. More specifically, the radiation can have a wavelength between 150 and 270 nm, or between 170 and 230 nm. Over this wavelength range, the energy of an individual photon is between approximately 5.5 and 7.5 eV (or 130 and 175 kcal/mole). This greatly exceeds the thermal energies at the temperatures typically employed for thermal sampling, between 100 and 250° C. (0.030-0.045 eV).

Furthermore, the method for incorporation of the directed energy source within an apparatus that allows the chemicals volatilized by exposure to the radiation either to be captured on an intermediate surface for subsequent vaporization into the detector or to be directly desorbed into the detector. Also, the apparatus can be a general-purpose chemical sampler and, has no restrictions on the type of chemical detector with which it is integrated. Rather, the described sampling method can be used in conjunction with virtually any chemical detector, including, for example, an ion mobility spectrometer, a gas chromatograph, a mass spectrometer, a gas-phase infrared spectrometer, a chemiluminescence-based detector, a fluorescence detector, a fluorescence-quenching detector, a flame ionization detector, an infrared spectrometer, a chemiresistive detector, an artificial nose, a fast gas chromatograph, and a surface acoustic wave device.

The details of one or more embodiments are set forth in the accompanying drawings and the description below. Other features, objects, and advantages will be apparent from the description and drawings, and from the claims.

DETAILED DESCRIPTION

Figure 1A:
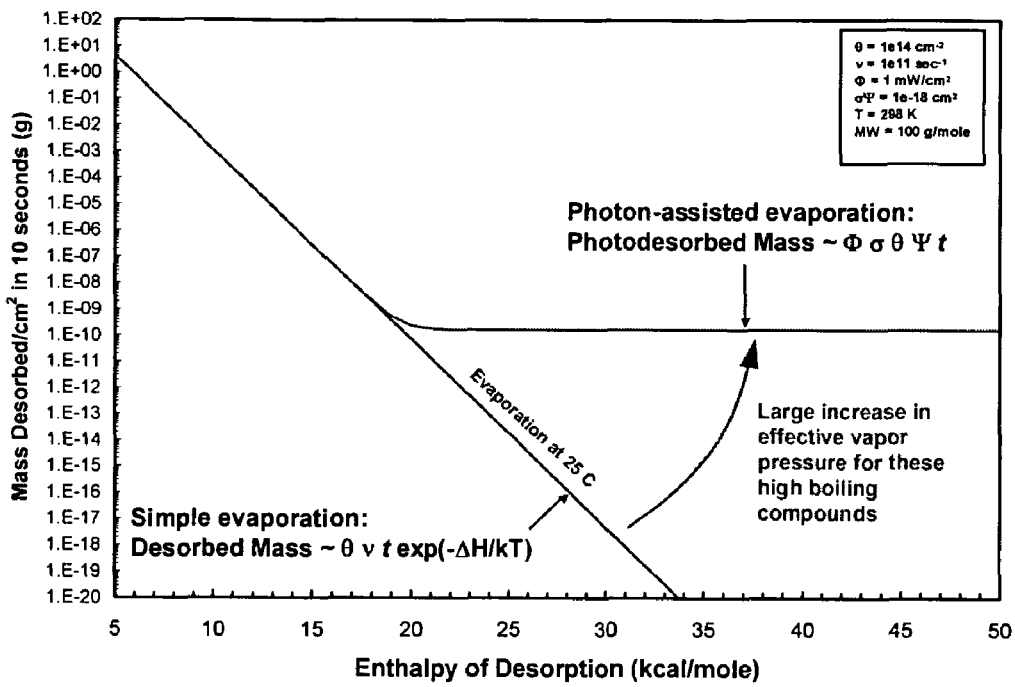
FIGS. 1a and 1b are graphs showing calculated evaporation rates under thermal and photonic activation.

A method for collecting and concentrating trace chemicals for subsequent analysis by virtually any type of chemical detector is described. Directed electromagnetic radiation increases the evaporation rates of chemicals, thereby rendering the chemicals more easily detected. The wavelength of the irradiation can be between 150 and 220 nm and virtually any type of sample or surface is irradiated in close proximity to the radiation source while the gas flow over the sample is controlled. For example, the sample can be a piece of paper, such as currency, or an article of clothing. The photo-evaporated products can be directed into a concentration chamber before further analysis. The actual analysis can be performed using any molecular detector, an ion mobility spectrometer, a surface acoustic wave device, an artificial nose, a fast gas chromatograph, a chemiluminescence-based detector, a fluorescence or fluorescence-quenching detector, a flame ionization detector, a flame photometric detector, or an infrared spectrometer.

Typical trace chemical detectors use heat in order to achieve measurable vapor pressures of tactically useful chemicals (explosives, controlled substances, etc.). The requirement for heat limits the types of samples that can be probed non-destructively and provides diminishing returns for very low vapor pressure compounds. Directed ultraviolet/ vacuum ultraviolet radiation activates non-thermal processes to shift the gas/solid equilibrium to what is in effect a much higher temperature. As a result, the ability of a chemical sensor to detect trace amounts of chemicals fixed on surfaces is enhanced.

Most analytical instruments measure chemicals in the gas phase. Instrument detection limits are driven in large part by the vapor pressure of the chemical to be detected. Heat is often employed to increase the vapor pressure and thus the limit of detection of a chemical with low vapor pressure at ambient temperature. The energy imparted to a molecule upon heating can be given by equation (1):

$$\text{Thermal energy upon heating} = k(T_2 - T_1) \quad (1)$$

where k is Boltzmann's constant and $T_1$ and $T_2$ are the initial and final temperatures, respectively. For typical levels of heating, this energy is generally on the order of 0.01 to 0.02 eV/molecule (0.25 to 0.50 kcal/mole). For molecules with enthalpies of vaporization in the 0.4 to 1.2 eV/molecule range (8 to 25 kcal/mole), this increase in thermal energy might increase the equilibrium vapor pressure by a factor of $10^3$ to $10^7$, as described by the Arrhenius Equation (2).

$$\text{Evap Rate} \sim \nu \exp(-E_a/kT) \quad (2)$$

Although these numbers may seem large, the room temperature vapor pressures of some compounds are so low ($<10^{-8}$ Torr), that only by heating to the highest practical temperatures ($>200°$ C.) is there any chance of trace detection. The use of heat to vaporize an analyte can suffer serious limitations. It may not be practical to heat the suspect sample to sufficiently high temperatures. For example, the chemical may be on an individual's clothing, luggage, or other delicate personal artifact, or large items may need to be tested, such as floorboards in an aircraft, the metal lining of an automobile trunk, household countertops, etc. In these cases, the suspect sample must be mechanically wiped or vacuumed to collect particulate matter, which can then be heated remotely from the suspect sample. This can be effective if chemically tainted particles exist but can be less effective or ineffective if the trace chemicals exist only as molecular layers or as entrained particles. Furthermore, not all tactically useful chemicals exist in their physisorbed state, and hence they do not follow the usual gas-surface equilibrium described by equation (2). Chemicals may be covalently bound to a surface, for instance, or entrained within a fiber or cavity within a surface. In these circumstances, an activation energy greater than that provided by simple heating (described in equation (1)) is needed to achieve useful vapor pressures.

Figure 1B:
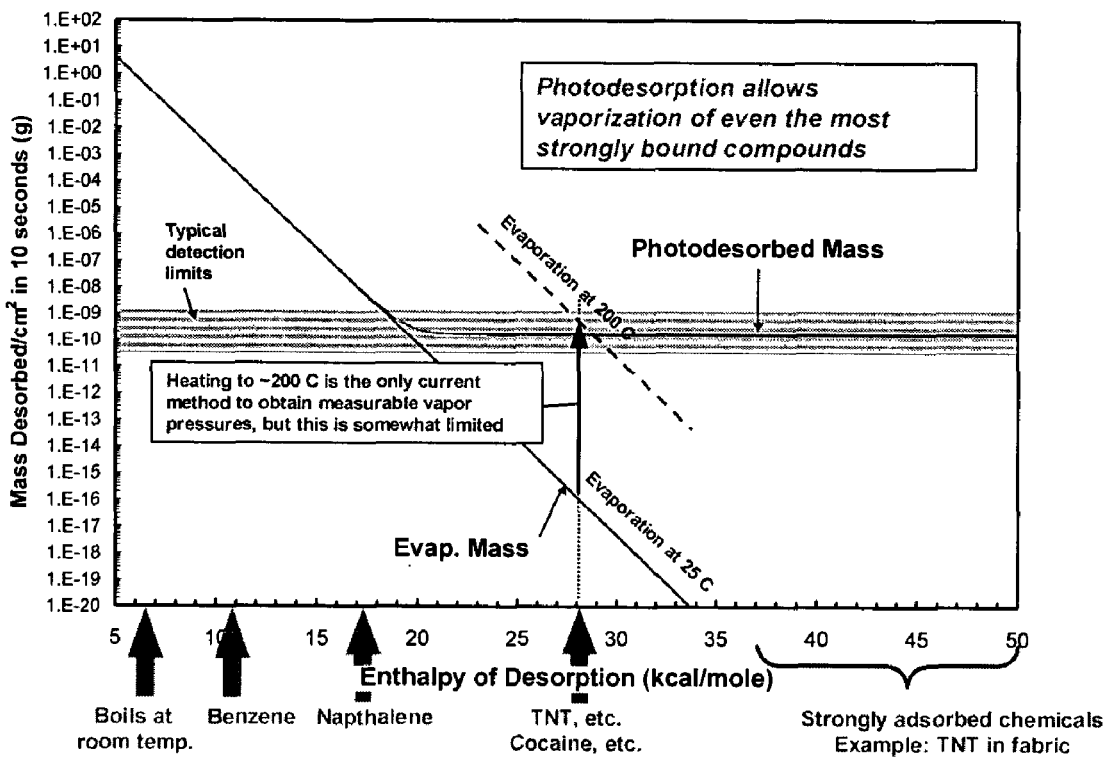

FIG. 1 shows calculated evaporation rates under thermal and photonic activation for typical but hypothetical conditions. FIG. 1a depicts a comparison of desorption rates for thermally activated evaporation at 25° C. and evaporation enhanced by photon assisted desorption, both as a function of heat of vaporization. FIG. 1b superimposes heats of vaporization for certain compounds and the thermally activated evaporation rate at 200° C. onto FIG. 1a. Note that for the highest heats of vaporization, heating alone cannot increase the evaporation rates to match the detection limits of a hypothetical instrument.

The sample can be an arbitrary surface, or it can be a specific surface upon which a particulate or aerosol sample has been collected. A sample can include an article of commerce, or items that can be bought or sold. Examples include consumer goods, such as clothing or books. An aerosol sample can be collected with a particle impactor, such as the ThermoAndersen Cascade, TSI Incorporated Model 3306 or 8522, Moudi Model 100, the Harvard impactor, or equivalent.

A photon source can irradiate the surface or sample being tested. The photon source can provide UV or VUV radiation. The photon source can be a laser or non-laser source. The radiation wavelength can be between 100 and 400 nm, preferably between 150 and 270 nm, more preferably 170 and 230 nm. The sample can be irradiated for 1 to 100 seconds at a lamp irradiance of 0.1 to 1000 mW/cm$^2$. The area irradiated can be between 0.1 and 100 cm$^2$. Irradiation of a sample can vaporize an analyte without ionizing the analyte. The vapor or gas evolved as a result of irradiation is generated in a vaporization space, or headspace. The headspace can be at ambient temperature, that is, the same temperature as its surroundings, such as room temperature. The headspace can be at a temperature other than ambient temperature, such as a temperature less than 100° C. The headspace can be at ambient pressure, such as atmospheric pressure. The gas in the headspace can be collected in such a fashion that little, if any, of it is allowed to escape to the surroundings outside the instrument. The collected headspace gas can be either directly introduced into a chemical detector (direct sampling), or alternatively is directed into a trap where it is collected for subsequent analysis (preconcentration). Preconcentration methods to trap the headspace vapors include the use of chilled surfaces, sorptive polymers (e.g., Tenax), and/or permeable membranes (e.g., silicone). Either collection method can be used to detect an analyte. A carrier gas can be present in the headspace. The carrier gas, for example air or an inert gas, can help move the analyte vapor to the detector. The chemical detector used is not limited to any specific type. The chemical detector can be, but is not limited to, an ion mobility spectrometer, a surface acoustic wave device, an artificial nose (for example as described in U.S. Pat. No. 6,368,558, incorporated herein by reference), a fast gas chromatograph, a chemiluminescence-based detector, a fluorescence or fluorescence-quenching detector, a flame ionization detector, a flame photometric detector, an infrared spectrometer, or micro field-asymmetric ion mobility spectrometer (for example as described in U.S. Pat. No. 6,495,823, incorporated herein by reference). A surface acoustic wave device is an extremely sensitive gravimetric detector that can be coated with a film that responds to chemical species of interest. Chemiluminescence is the generation of light upon the reaction of an analyte with a light-producing reagent. A fluorescence or fluorescence-quenching detector can respond to the fluorescence of an analyte or to changes in fluorescence upon interaction of an analyte with a fluorophore. A flame photometric detector can detect light emitted by an analyte as it passes through a flame.

Many types of chemicals can be detected. Classes of chemicals that can be detected include, for example, solvents, explosives, explosive residues, drugs, poisons, and pollutants. Multiple analytes can be vaporized and detected from a single sample. Samples can be distinguished by the identities and/or abundances of analytes detected. See Example #3 below.

The UV radiation can vaporize an analyte molecule via photoscission of the molecule into smaller, more volatile, and hence more easily detected fragments. The headspace vapor can include photoscission products, and not just chemicals in the original sample, as long as the specific signature of analyte photodegradation is known. Photochemically active reagents can be added to the original sample to assist in the creation of unique, volatile signatures of the analyte. A photon can create a detectable headspace vapor via direct vaporization, photoscission, or photoreaction with another molecule. See Example #5 below.

Figure 2:
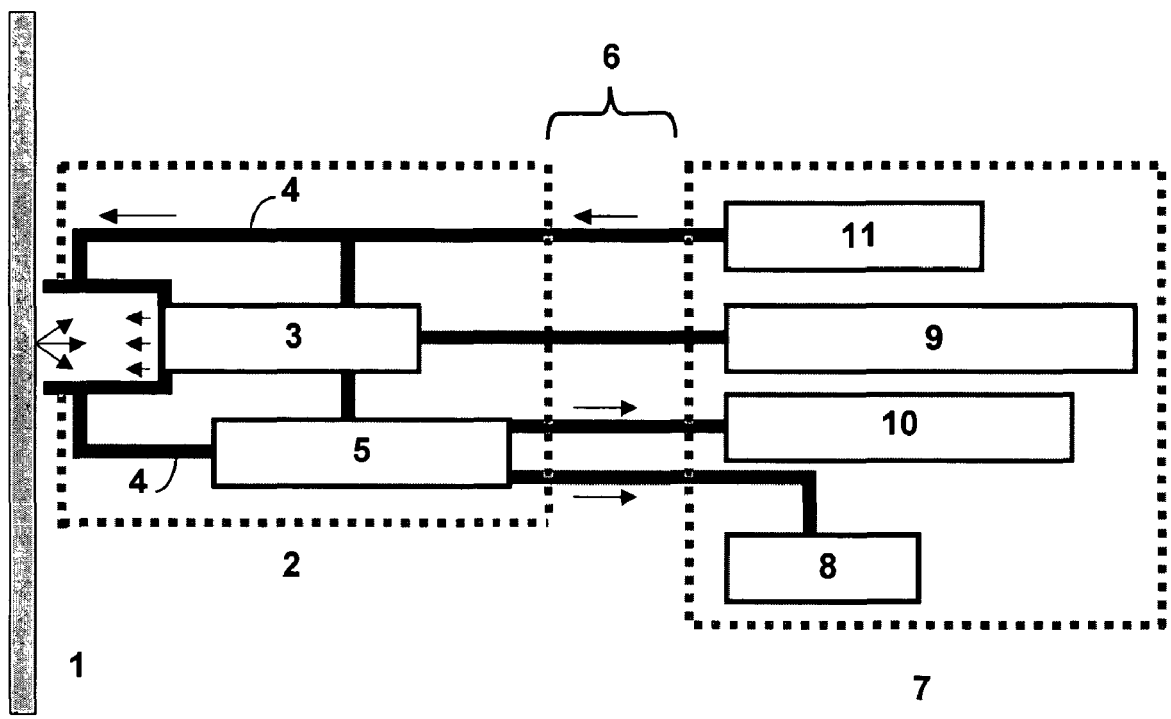
FIG. 2 is a schematic diagram depicting an apparatus including a directed radiation sampler.

A schematic of an apparatus appears in FIG. 2. A sample or surface 1 to be tested is in close proximity to a sampling body 2. The sampling body includes a radiation source 3, tubing 4 both to control the composition of the headspace gas and to collect the headspace gas, and an optional preconcentrator 5. This sampling body can be connected to the main instrument body via a cable bundle 6. The main instrument body 7 houses the detector 8, the power supply 9, sampling pump 10, and an optional purge gas source 11.

Figure 7:
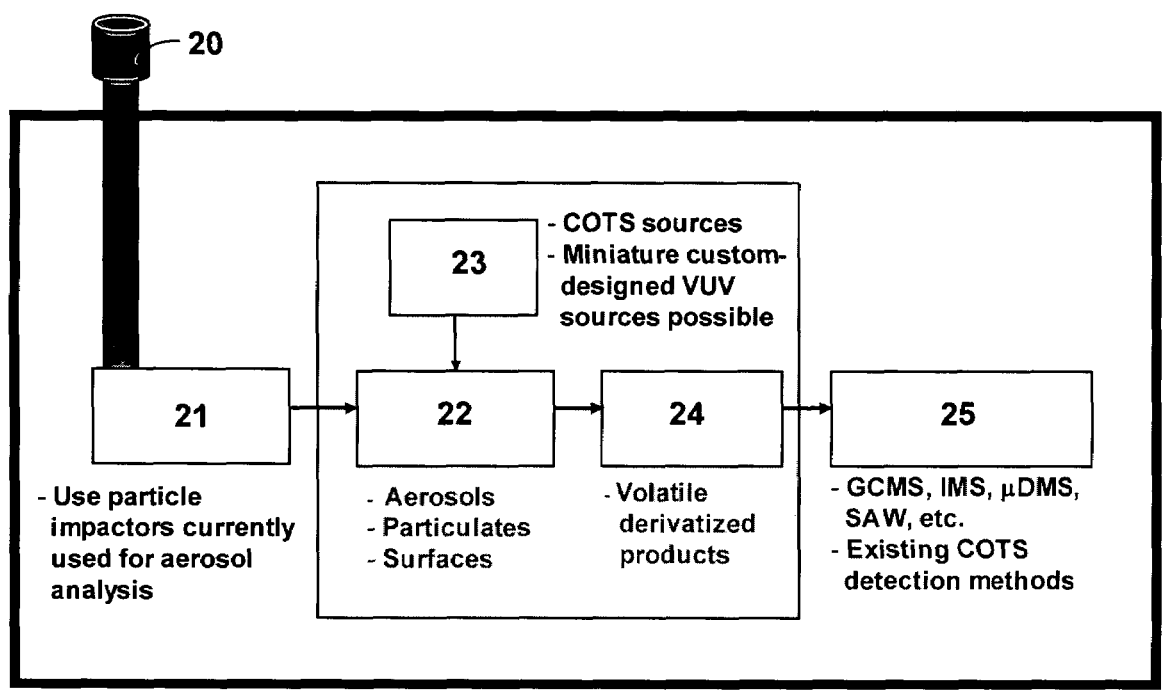
FIG. 7 is a schematic diagram depicting an apparatus including an apparatus including an aerosol sampler.

FIG. 7 is a schematic of an apparatus configured to sample aerosols. An aerosol stream 20 impacts particles onto a surface using a particle impactor 21. The impacted particles on the surface form a sample 22. The sample is illuminated by a UV or VUV radiation source 23 to generate a headspace vapor 24 from the collected aerosols. This headspace vapor is then flowed into a chemical sensor 25 where an analyte can be detected.

The sampler can be portable, that is, of sufficiently small size and weight that it can be carried by an individual. In certain circumstances, the sampler can be hand-held. The sampler and an associated detector can also be portable or hand-held.

EXAMPLE #1

Figure 3:
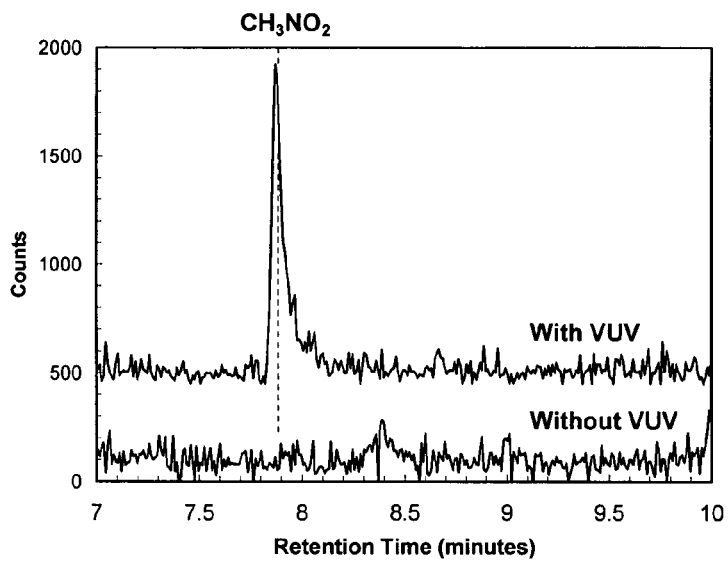
FIG. 3 is a graph depicting a gas chromatogram of head space gas generated by a sample with and without directed radiation.

FIG. 3 depicts the results of two tests performed with and without the presence of 172 nm radiation. The detector was a gas chromatograph-mass spectrometer. The sample was a woman's shoe sole contaminated with 250 nanograms of dinitrotoluene (DNT), 250 nanograms of pentaerythritol tetranitrate (PETN), and 250 nanograms of hexahydro-1,3,5-trinitro-1,3,5-triazine (RDX). Under these conditions, the radiation produced an increased flux of a photolysis byproduct, methyl nitrate, which could render these chemicals more easily detected.

EXAMPLE #2

Figure 4:
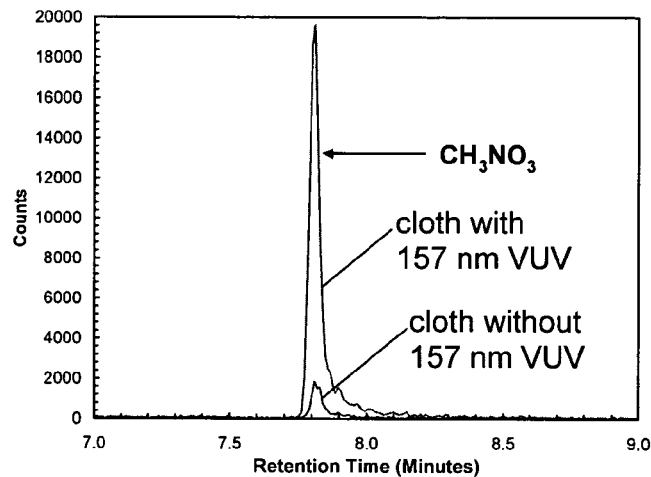
FIG. 4 is a graph depicting a gas chromatogram of head space gas generated by a sample with and without directed radiation.

FIG. 4 depicts the results of two tests performed with and without the presence of 157 nm radiation. The detector was a gas chromatograph-mass spectrometer. The sample was a piece of linen fabric contaminated with 25 micrograms of RDX. Under these conditions, the radiation produced an increased flux of decomposition product, methyl nitrate, which could render this chemical more easily detected.

EXAMPLE #3

Figure 5:
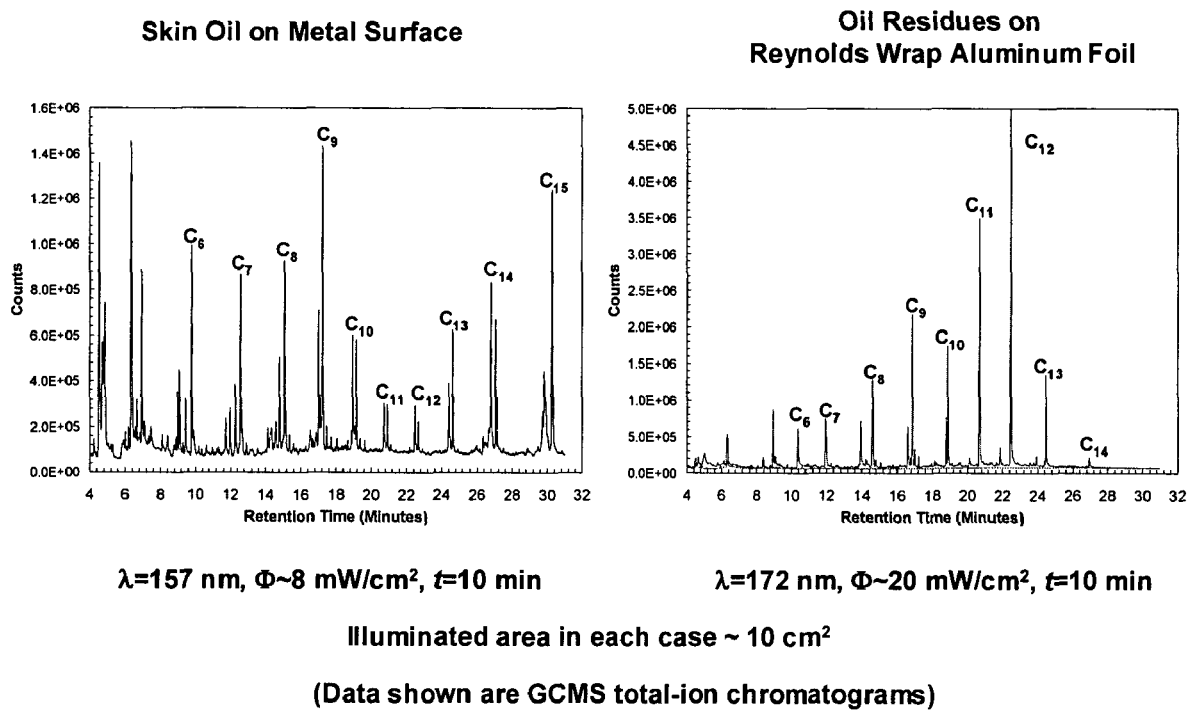
FIG. 5 is a pair of graphs depicting gas chromatograms of head space gas generated by exposing oil samples on metal surfaces to directed radiation.

FIG. 5 depicts the results of two separate analyses performed on oil-contaminated surfaces. On the left is human skin oil obtained by contact of the sample with human skin, whereas the analysis on the right is the residual oil on commercial aluminum foil. Both samples were at room temperature during the measurement and showed no signal without radiation. Mid-and low-volatility compounds can be vaporized by using this technique. For example, the component labeled C15 in FIG. 5 has a boiling point of ~270° C. and a heat of vaporization of ~15 kcal/mole. Compositions can be distinguished using this technique by virtue of the individual chemicals that are volatilized. Under these conditions, arrayed detection such as that used in artificial noses can be used to distinguish materials.

EXAMPLE #4

Figure 6:
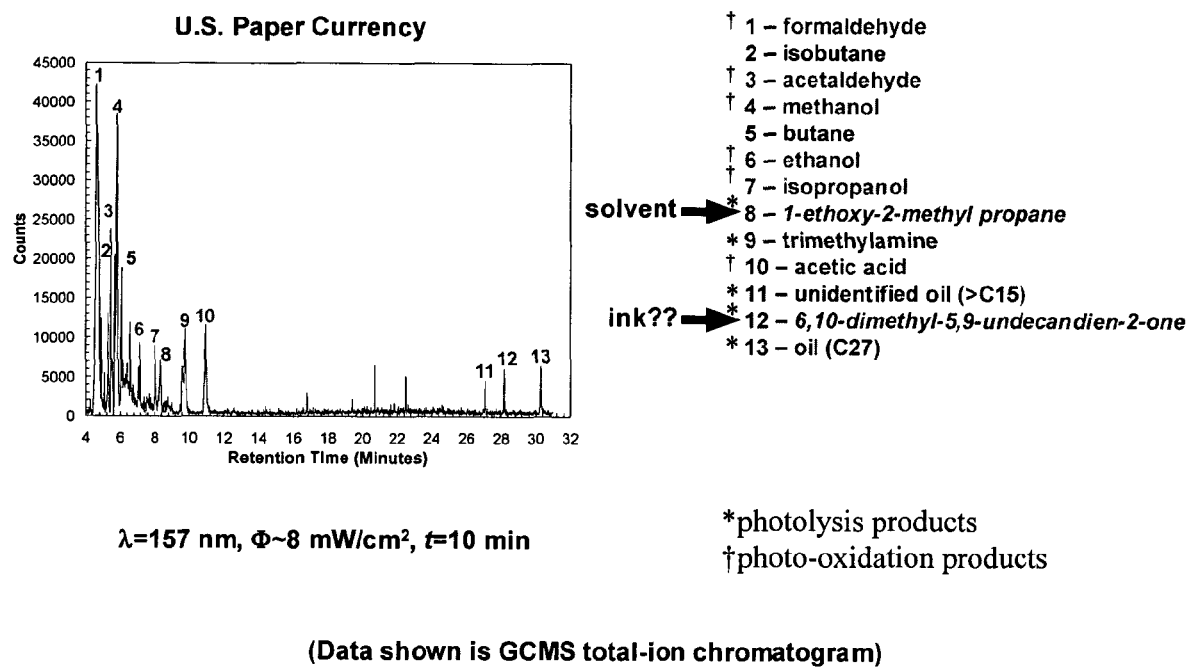
FIG. 6 is a graph depicting a gas chromatogram of head space gas generated by exposing a piece of currency to directed radiation.

FIG. 6 depicts the results of an analysis performed on a United States $20 bill. This technique could be used to authenticate currency, art work, or other valuable documents by virtue of the presence of specific chemicals. Such analysis, where the activating radiation penetrates no more than ~0.1 micron, cannot be performed non-destructively as readily using thermal activation.

EXAMPLE #5

Figure 8:
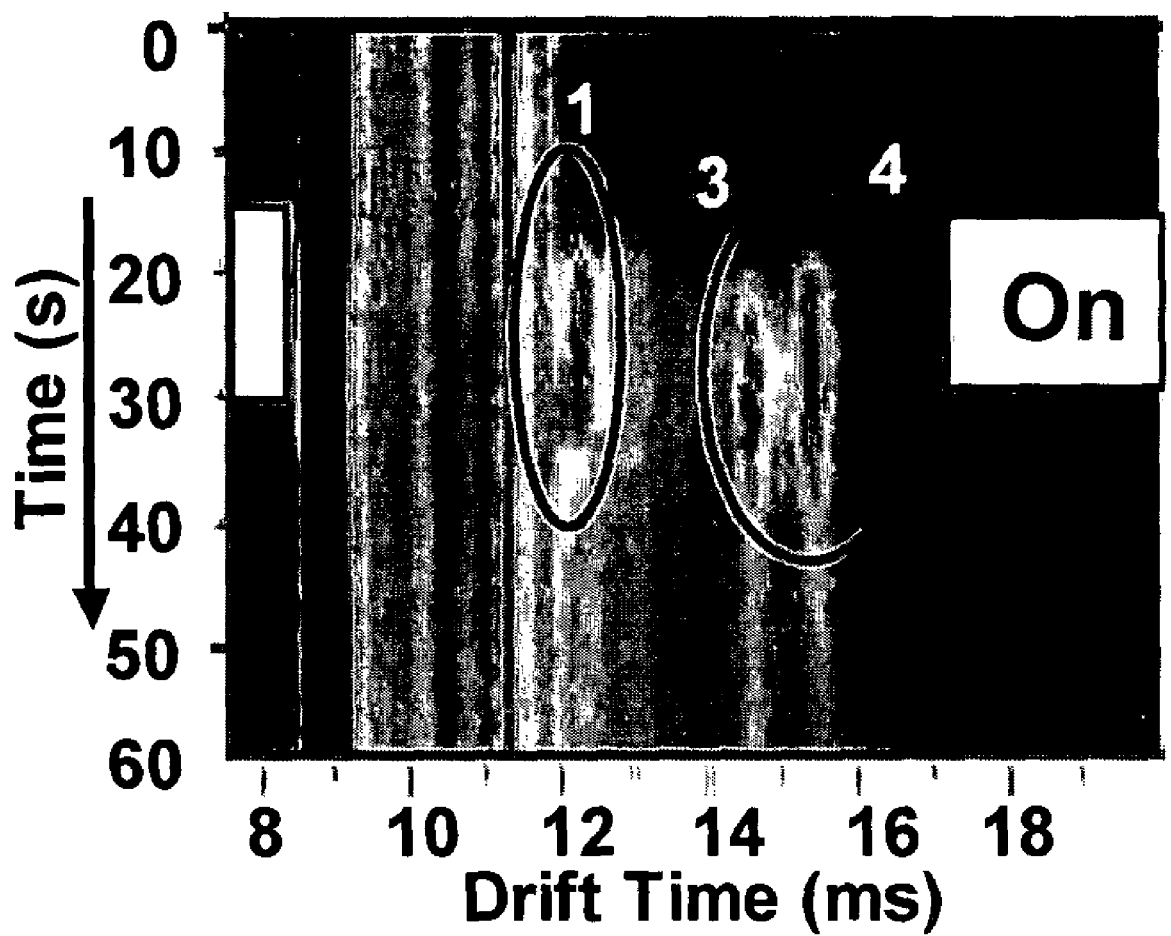
FIG. 8 is a graph depicting ion mobility spectra recorded before, during and after UV illumination of an impacted aerosol sample.

FIG. 8 depicts the signal generated from a 1 mg sample of Arizona road dust contaminated with ~0.01% (~200 nanograms) of malathion pesticide. The dust was analyzed with an apparatus of the type depicted in FIG. 7. The detector was an ion mobility spectrometer and data were collected for 60 seconds (y-axis, descending). The UV source was a 222 nm lamp, lit between 15 and 30 seconds during data collection (box labeled "On" in FIG. 7). Three of the four major photolysis by-products of malathion generated by the 222 nm radiation were detected. These peaks are labeled 1, 3, and 4. Chemical contaminants, such as pesticides or other harmful compounds present in aerosols at low levels, can be detected and identified.

Other embodiments are within the scope of the following claims.

What is claimed is:

1. A method comprising:
providing a sample;
irradiating the sample using electromagnetic radiation with a wavelength in a range from 150 nm to 270 nm and at an irradiance of 0.1-1000 mW/cm2, wherein the radiation increases an evaporation rate of an analyte within the sample, thereby causing vaporization of the analyte from the sample;
capturing the vaporized analyte in a vaporization space; and
detecting the vaporized analyte with a detector.

2. The method of claim 1, wherein the wavelength of the radiation is in a range from 170 nm to 230 nm or in a range from 150 nm to 220 nm.

3. The method of claim 1, wherein the vaporization space is at ambient pressure.

4. The method of claim 1, wherein the vaporization space is at a temperature less than 100° C.

5. The method of claim 1, wherein irradiating the sample comprises irradiating the sample using a non-laser radiation source.

6. The method of claim 1, wherein irradiating the sample comprises irradiating the sample using a laser radiation source.

7. The method of claim 1, further comprising concentrating the vaporized analyte before detecting the analyte.

8. The method of claim 7, wherein the analyte is concentrated using a chilled surface, a sorptive polymer, or a permeable membrane.

9. The method of claim 1, wherein a charge of a molecule of the analyte vapor is the same as a charge of a molecule of the analyte.

10. The method of claim 1, wherein detecting the vaporized analyte comprises transporting the analyte vapor to a detector with a carrier gas.

11. The method of claim 10, wherein the carrier gas is air.

12. The method of claim 10, wherein the carrier gas is an inert gas.

13. The method of claim 1, wherein the sample is an article of commerce.

14. The method of claim 1, wherein the sample comprises a non-volatile material.

15. The method of claim 1, wherein the radiation is applied from a radiation source in a sampling unit, the sampling unit comprising the vaporization space, wherein gas in the vaporization space can be collected in such a fashion that little if any is allowed to escape into the surrounding environment.

16. The method of claim 15, wherein the sampling unit is portable.

17. The method of claim 15, wherein the sampling unit is positioned over a surface of the sample so that an opening on the sampling unit is located over an area of the sample to be analyzed.

18. The method of claim 1, wherein the analyte is detected using an ion mobility spectrometer, a surface acoustic wave device, an artificial nose, a gas chromatograph, a chemiluminescence detector, a fluorescence detector, a fluorescence-quenching detector, a flame ionization detector, a flame photometric detector, or an infrared spectrometer.

19. The method of claim 1, wherein the sample comprises paper, wood, plastic, metal, or fabric.

20. The method of claim 1, wherein the sample is an article of clothing.

21. The method of claim 1, wherein the analyte is a drug.

22. The method of claim 1, wherein the analyte is an explosive or a residue of an explosive.

23. The method of claim 1, wherein the analyte is a poison or a pollutant.

24. The method of claim 1, wherein the sample comprises an aerosol particle.

25. The method of claim 24, wherein providing the sample comprises collecting the aerosol particle on a surface to form the sample.

26. The method of claim 1, wherein the radiation is vacuum ultraviolet (VUV) radiation.

27. The method of claim 1, wherein the sample is irradiated for 1-100 seconds.

28. The method of claim 1, wherein an area of the surface irradiated with the electromagnetic radiation is 0.1-100 $cm^2$.

29. The method of claim 1, wherein vaporization is non-thermal.

30. The method of claim 1, wherein capturing the analyte comprises capturing the analyte on an intermediate surface.

31. The method of claim 1, wherein the vaporization space can include additional products not present in the sample.

32. The method of claim 1, wherein the sample comprises more than one analyte.

* * * * *

UNITED STATES PATENT AND TRADEMARK OFFICE
CERTIFICATE OF CORRECTION

PATENT NO. : 7,687,276 B2
APPLICATION NO. : 10/443141
DATED : March 30, 2010
INVENTOR(S) : Roderick R. Kunz It is certified that error appears in the above-identified patent and that said Letters Patent is hereby corrected as shown below:

On the First Page, Column 1 (Title), line 3, delete "LOW-POWER" and insert -- LOW POWER --

In Column 1, line 3, delete "LOW-POWER" and insert -- LOW POWER --

In Column 7, line 29, in claim 1, delete "mW/cm2," and insert -- $mW/cm^2$, --

Signed and Sealed this

Eighth Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,687,276 B2 | Page 1 of 1 |
| APPLICATION NO. | : 10/443141 | |
| DATED | : March 30, 2010 | |
| INVENTOR(S) | : Roderick R. Kunz | |

It is certified that error appears in the above-identified patent and that said Letters Patent is hereby corrected as shown below:

Please delete the paragraph titled 'FEDERALLY SPONSORED RESEARCH OR DEVELOPMENT, encompassing column 1, lines 14-16:

"The U.S. Government may have certain rights in this invention pursuant to Grant No. F19628-00-C-0002 awarded by the Department of the Air Force."

and replace with:

--This invention was made with government support under Contract No. F19628-00-C-0002 awarded by the U.S. Air Force. The government has certain rights in this invention.--

Signed and Sealed this
Sixteenth Day of October, 2012

David J. Kappos
*Director of the United States Patent and Trademark Office*